United States Patent
Harms et al.

(10) Patent No.: US 12,147,570 B2
(45) Date of Patent: Nov. 19, 2024

(54) SIMULTANEOUSLY ADMINISTERING USER ACCOUNTS IN TWO RELATED INFORMATION SYSTEMS, SUCH AS AN EMR AND A SEPARATE HEALTH SYSTEM SINGLE SIGNON SYSTEM

(71) Applicant: Providence St. Joseph Health, Seattle, WA (US)

(72) Inventors: Trevor A. Harms, Surrey (CA); Tripurari Dash, Hyderabad (IN); Robin Kang, Prosper, TX (US); Colin M. Dere, Calgary (CA); Lisa D. Mason, Newcastle, WA (US); Sainikhil Manda, Hyderabad (IN)

(73) Assignee: Praia Health Inc., Renton, WA (US)

( * ) Notice: Subject to any disclaimer, the term of this patent is extended or adjusted under 35 U.S.C. 154(b) by 155 days.

(21) Appl. No.: 18/164,190

(22) Filed: Feb. 3, 2023

(65) Prior Publication Data
US 2024/0265129 A1 Aug. 8, 2024

(51) Int. Cl.
G06F 21/62 (2013.01)
G16H 10/60 (2018.01)

(52) U.S. Cl.
CPC ......... G06F 21/6245 (2013.01); G16H 10/60 (2018.01)

(58) Field of Classification Search
CPC ............................ G16H 10/60; G06F 21/6245
See application file for complete search history.

(56) References Cited

U.S. PATENT DOCUMENTS

| 2004/0078236 A1* | 4/2004 | Stoodley | G16H 70/20 705/2 |
| 2009/0326972 A1* | 12/2009 | Washington | G06Q 10/10 705/1.1 |
| 2015/0244687 A1* | 8/2015 | Perez | G16H 10/60 726/4 |

(Continued)

FOREIGN PATENT DOCUMENTS

WO 2014-134604 A1 9/2014

OTHER PUBLICATIONS

NPL Search Terms (Year: 2024).*
International Search Report and Written Opinion, PCT/US2024/014300, Jun. 3, 2024, 7 pages.

*Primary Examiner* — Syed A Zaidi
(74) *Attorney, Agent, or Firm* — Seed Intellectual Property Law Group LLP (57) ABSTRACT

A facility applies a received query containing identifying information for a person to both (1) first accounts in a first information system each authorizing access to a resource among a set, to obtain a first result identifying any matching first accounts; and (2) second accounts in a second information system that each authorize access to a resource among the set, to obtain a second result identifying any matching second accounts. For each resource of the set whose access is authorized by at least one identified first account or one identified second account, the facility creates an entry representing any identified first account authorizing access to the resource and any identified second account authorizing access to the resource. The facility causes the created entries to be displayed, and solicits input selecting a displayed entry for administrative action with respect to at least one of the accounts it represents.

18 Claims, 8 Drawing Sheets

(56) References Cited

U.S. PATENT DOCUMENTS

| | | |
|---|---|---|
| 2015/0379198 A1 | 12/2015 | Tabmasco, Jr. |
| 2016/0085914 A1* | 3/2016 | Douglass ............... G16H 10/60 705/3 |
| 2017/0147755 A1 | 5/2017 | Lim et al. |
| 2018/0107794 A1 | 4/2018 | Fierer et al. |
| 2018/0196920 A1 | 7/2018 | Liang et al. |
| 2020/0294642 A1* | 9/2020 | Bostic ................... G16H 50/20 |

* cited by examiner

| EMR username | EMR email | EMR password | name | last 4 SSN | DOB | EMR record ID |
|---|---|---|---|---|---|---|
| msims@outlook.com | msims@outlook.com | **** | Marcus Sims | 5662 | 2/1/2001 | 3800415563 |
| ARWinters | ARWinter@yahoo.com | **** | Alice Winters | 8523 | 4/1/1980 | 20005468017 |
| BestPatient | some_email@email.com | **** | William Baskar | 3532 | 1/1/2015 | 6000434599 |
| ... | | | | | | |

EMR accounts table (WAMT) 400

411, 412, 413, 414, 415, 416, 417
401, 402, 403

*FIG. 4* health system accounts table 500

| health system account sign-in name | password | health system account ID | |
|---|---|---|---|
| bestpatient | **** | 9186253401 | — 501 |
| BaskarW | **** | 2105435498 | — 502 |
| ⋮ | | | |
| 511 | 512 | 513 | |

FIG. 5

EMR link table 600

| health system acct ID | EMR instance ID | EMR record ID | |
|---|---|---|---|
| 2105435498 | WAMT | 60004434599 | — 601 |
| 9186253401 | AK | 1130525 | — 602 |
| 9186253401 | WAMT | 20005468017 | — 603 |
| ⋮ | | | |
| 611 | 612 | 613 | |

SIMULTANEOUSLY ADMINISTERING USER ACCOUNTS IN TWO RELATED INFORMATION SYSTEMS, SUCH AS AN EMR AND A SEPARATE HEALTH SYSTEM SINGLE SIGNON SYSTEM

BACKGROUND

Electronic medical records systems ("EMRs," also referred to as electronic health record systems, "EHRs") store, display, and exchange information about patients. The information stored by an EMR about a particular patient is referred to as a record. It is common for EMRs to establish accounts for patients that they can use to view and interact with the information in their records via the web or a smartphone app.

As part of establishing an account for a patient, an EMR typically collects and stores the patient's email address—or other sign-in name—and a password. The EMR creates a mapping from the patient's sign-in name to an internal identifier used by EMR to access the patient's EMR record.

To access his or her record, a patient inputs his or her sign-in name and password into a web form or smartphone app, which forwards them to the EMR. The EMR authenticates the patient, uses the mapping to identify his or her record, and provides access to that record via the web browser or smartphone app.

DETAILED DESCRIPTION

The inventors have recognized a number of disadvantages in the ways that patients conventionally access their EMR data via EMR accounts. In some cases, a single health system operates multiple EMR instances, such as when a health system maintains different EMR instances for different geographic regions. In such cases, a patient must select the correct instance on which to establish an account, navigate to that instance to establish the account, and later navigate to that instance to login to the account and access the data in the instance. This issue is compounded where multiple instances contain records for the same patient, such as for a patient who has received care from the health system in multiple geographic regions. Such patients must manage different login credentials for each of the instances that store their data, and navigate to the correct instance to sign in.

In response, some health systems have established a single signon system that allows each patient to sign into any information system operated by the health system, including any of the health system's EMR instances, using a single health system account. Such single signon systems include those described in U.S. Provisional Patent Application No. 63/293,969, filed Dec. 27, 2021; U.S. patent application Ser. No. 17/589,084, filed Jan. 31, 2022; and U.S. patent application Ser. No. 18/056,189, filed Nov. 16, 2022, each of which is hereby incorporated by reference in its entirety. In cases where the present application and a document incorporated by reference disagree, the present application controls.

To assist patients with setting up and troubleshooting both (1) the patients' health system accounts, and (2) their EMR records and EMR accounts, a health system typically provides customer service agents with access to health system accounts via a dedicated health system account administration tool, and access to EMR records and EMR accounts via a separate EMR patient administration tool. The inventors have recognized that it is burdensome for customer service agents to have to use two separate administration tools to assist patients—often typing the same query into each to look up the patient they are helping—and further that this can cause errors in transcribing information between the two administration tools.

In response recognizing these disadvantages, the inventors have conceived and reduced to practice a hardware and/or software facility for simultaneously administering user accounts in two related information systems, such as an EMR and a separate health system single signon system ("the facility"). In some embodiments, the facility provides a user interface in which a facility user—such as a customer service agent working for a health system—can specify a single query that the facility uses to search user account data for both information systems. The facility then displays information about the accounts found in both information systems that match the query. From this point, in various embodiments, the user interface enables the facility user to review information stored for the patient in either or both information systems; change information stored for the patient in either or both information systems; create an account for the patient in one of the information systems using information stored for the patient in the other information system; reset one or both of their accounts' passwords; etc.

By operating in some or all of the ways described above, the facility allows a facility user to efficiently administer user accounts in two related information systems, by providing a single administration tool for launching a single query to find relevant accounts on both information systems, and taking actions in either or both information systems with respect to the results of the search that leverage the contents of both information systems.

Additionally, the facility improves the functioning of computer or other hardware, such as by reducing the dynamic display area, processing, storage, and/or data transmission resources needed to perform a certain task, thereby enabling the task to be permitted by less capable, capacious, and/or expensive hardware devices, and/or be performed with lesser latency, and/or preserving more of the conserved resources for use in performing other tasks. For example, by consolidating the input of a particular search into two separate user interfaces corresponding to health system accounts and EMR accounts into the input of the search into a single user interface provided by the facility, the facility eliminates the use of processing resources that would have been committed to operating a second user interface to receive a second copy of the query. By automatically transferring information between information systems, the facility eliminates the use of processing resources that would have been committed to resolving errors arising from manually transcribing the information between information systems.

Figure 1:
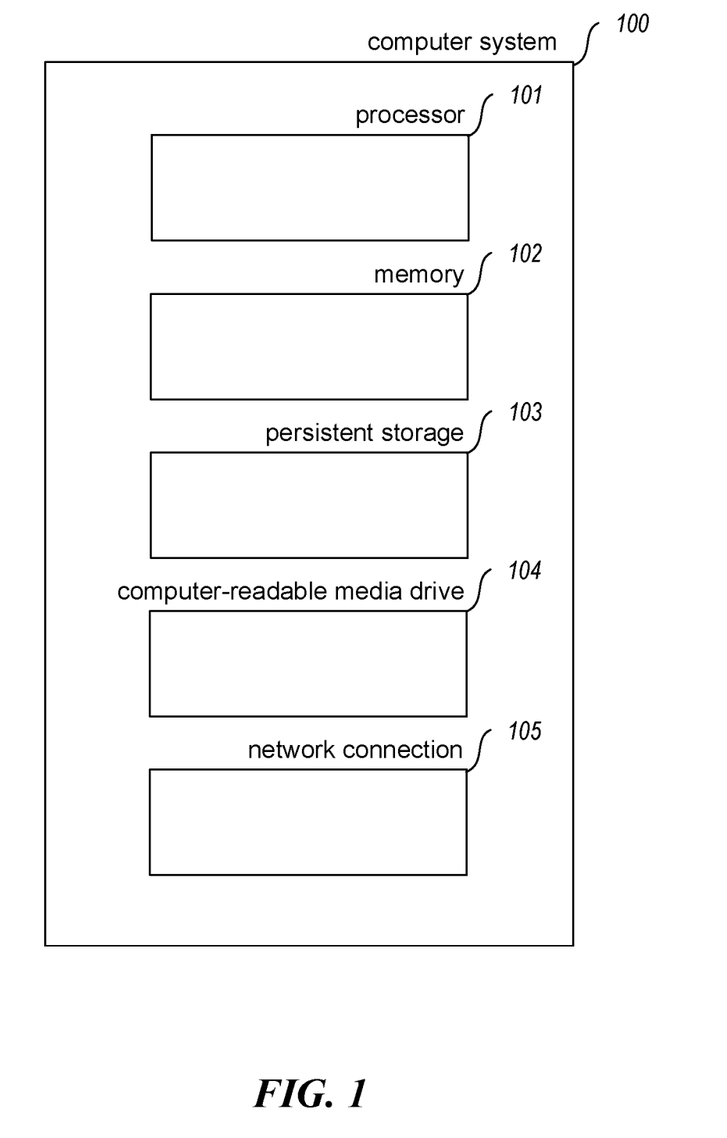
FIG. 1 is a block diagram showing some of the components typically incorporated in at least some of the computer systems and other devices on which the facility operates.

FIG. 1 is a block diagram showing some of the components typically incorporated in at least some of the computer systems and other devices on which the facility operates. In various embodiments, these computer systems and other devices 100 can include server computer systems, cloud computing platforms or virtual machines in other configurations, desktop computer systems, laptop computer systems, netbooks, mobile phones, personal digital assistants, televisions, cameras, automobile computers, electronic media players, etc. In various embodiments, the computer systems and devices include zero or more of each of the following: a processor 101 for executing computer programs and/or training or applying machine learning models, such as a CPU, GPU, TPU, NNP, FPGA, or ASIC; a computer memory 102 for storing programs and data while they are being used, including the facility and associated data, an operating system including a kernel, and device drivers; a persistent storage device 103, such as a hard drive or flash drive for persistently storing programs and data; a computer-readable media drive 104, such as a floppy, CD-ROM, or DVD drive, for reading programs and data stored on a computer-readable medium; and a network connection 105 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 2:
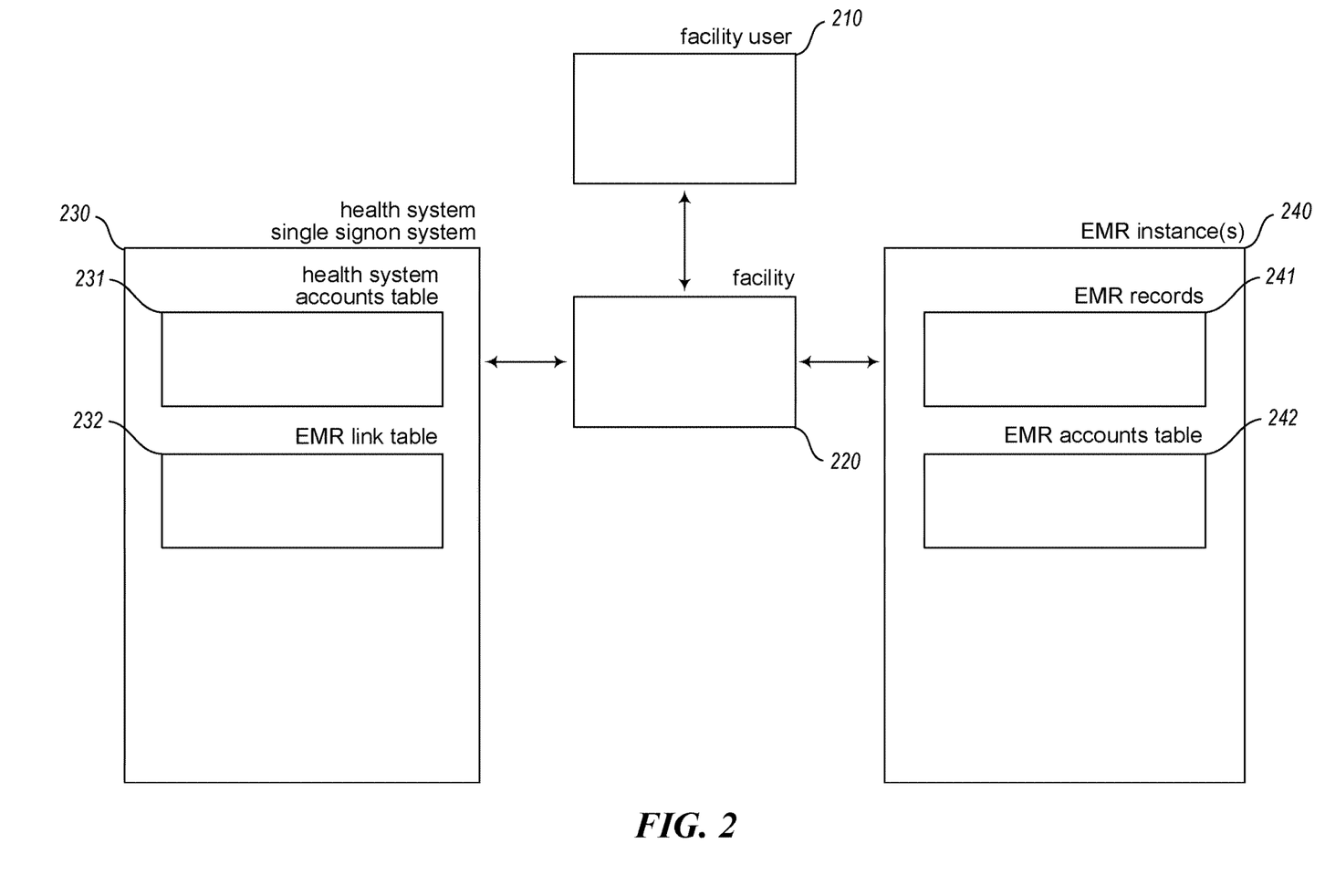
FIG. 2 is showing an environment in which the facility operates in some embodiments.

FIG. 2 is showing an environment in which the facility operates in some embodiments. The diagram shows a facility user computing system 210 with which a facility user interacts with the facility. In some embodiments, facility users are customer service agents working for a health system to assist patients with the patients' accounts, including patients' EMR accounts in their health system single signon accounts. In various embodiments, the facility user computing system is of a variety of device types, including desktop computer system, laptop computer system, browser-based computer system, computer terminal, tablet or smartphone, etc. The facility user computing system interacts with the facility 220, which in turn interacts with a health system single signon system 230, as well as one or more EMR instances 240. In various embodiments, the facility is implemented using devices of various types, including one or more physical servers, virtual servers, cloud computing services, etc.

In some embodiments, the facility computing system interacts with the health system single signon system to search and/or modify tables maintained by the health system single signon system that contain state relating to patients' health system accounts. These include a health system accounts table 231 in which each row represents a different health system account, and includes a password for that health system account, as well as an internal identifier for that health system account; and an EMR link table in which each row connects any internal health system account identifier with an EMR record ID of an EMR record that the health system account is authorized to access, as well as an EMR instance ID instance identifying a particular EMR instance where that record resides. The facility further interacts with each of one or more EMR instances in order to search in and modify an EMR accounts table 242, in which each row represents a different EMR account that exists on the particular EMR instance, and contains such information about it as a password for the account, identifying information for the patient, and an EMR record ID for the EMR account that identifies a particular EMR record among the EMR records 241 that reside on the EMR instance.

Figure 3:
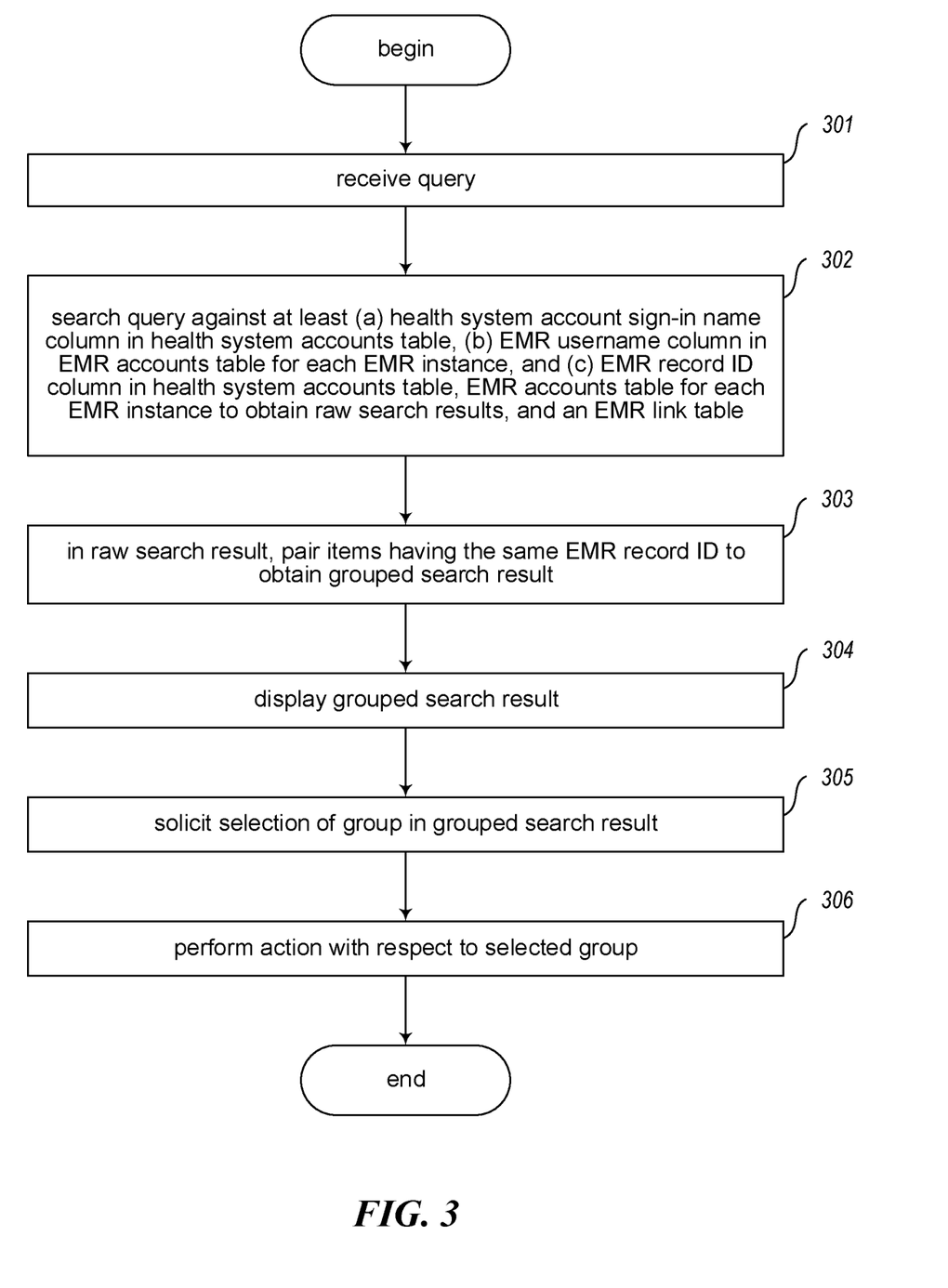
FIG. 3 is a flow diagram showing a process performed by the facility in some embodiments to maintain a group of accounts established for a particular patient.

FIG. 3 is a flow diagram showing a process performed by the facility in some embodiments to maintain a group of accounts established for a particular patient. In act 301, the facility receives a search query. In some embodiments, the facility displays a visual user interface that has a field into which the facility user can type the search query. In various embodiments, the facility supports a variety of other modalities for providing the query, including pasting it form a clipboard, speaking it, capturing an image of it, etc. In some embodiments, the query can contain any information that may be useful in identifying a particular patient on whose behalf the facility user is acting, and/or their health service account and/or their EMR account(s). As some examples, in some embodiments, the query can contain the person's name, their birthdate, part or all of their social security number, their email address, their health system account username, their EMR account username, a record identifier for one of their EMR records—such as an EPI identifier or an MRN identifier—a name or identifier for an EMR instance on which they have an EMR account and/or an EMR record, etc.

In act 302, the facility causes the query to be searched against at least the following data sources to obtain a set of raw search results: (a) portions of the health system account table such as the health system account sign-in name column; (b) portions of the EMR accounts table for each EMR instance, including the EMR username; (c) in a variety of tables such as the health system accounts table and the EMR accounts table for each EMR instance, portions that may contain an EMR record ID, such as the EMR record ID column of these tables; and (d) in an EMR link table that connects health services accounts to the EMR records that they are authorized to access. In act 303, in the raw search result produced in act 302, the facility pairs items having the same EMR record ID to obtain a grouped search result. In some embodiments, where a particular patient has EMR records on multiple EMR instances, a group can have more than two items. In act 304, the facility causes the grouped search result obtained in act 301 to be displayed to the facility user. In act 305, the facility solicits the facility user's selection of a particular group in the displayed grouped search result. In act 306, the facility performs an action with respect to one or more of the accounts represented in the group selected by the facility user. In some embodiments, the facility chooses this action automatically; in some embodiments, the facility chooses this action by displaying a list of available actions, and receiving user input selecting one. After act 306, this process concludes.

Those skilled in the art will appreciate that the acts shown in FIG. 3 may 3 may be altered in a variety of ways. For example, the order of the acts may be rearranged; some acts may be performed in parallel; shown acts may be omitted, or other acts may be included; a shown act may be divided into subacts, or multiple shown acts may be combined into a single act, etc.

Figure 4:
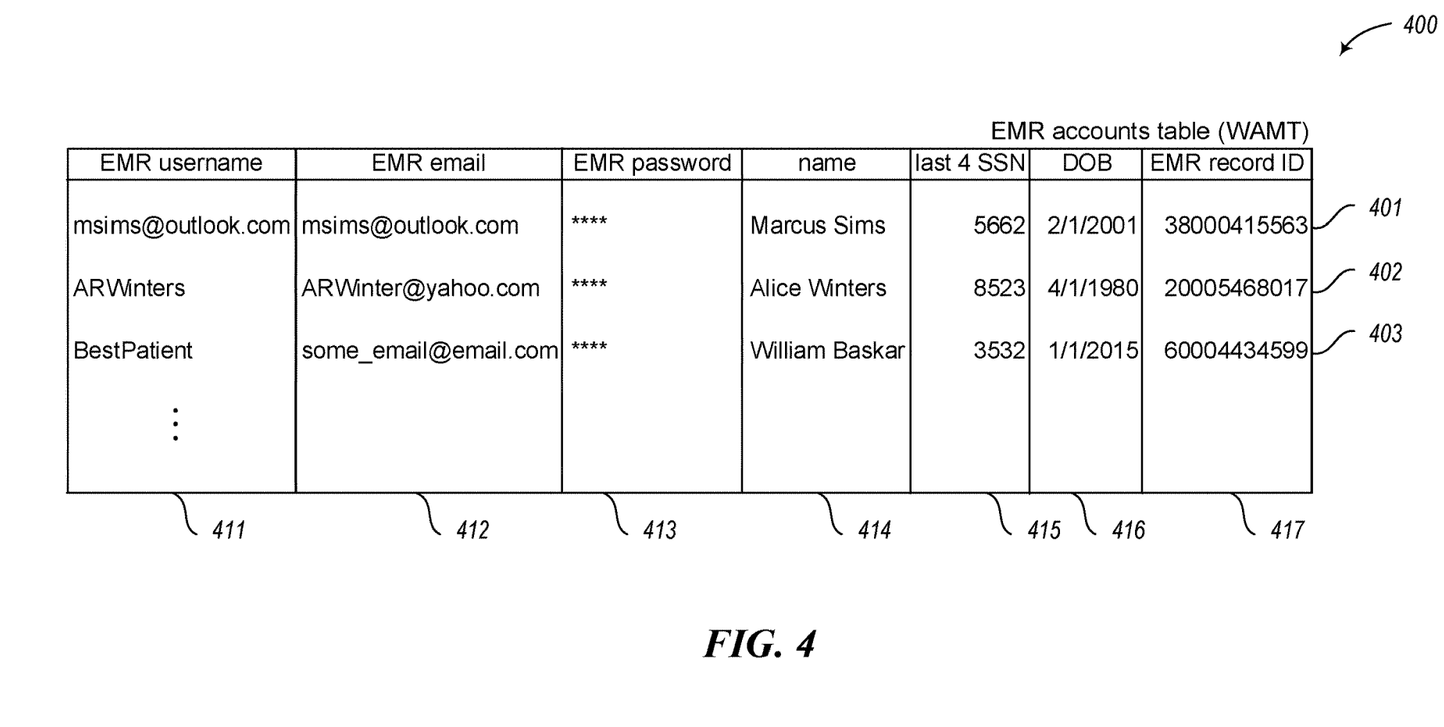
FIG. 4 is a table diagram showing sample contents of an EMR accounts table used by the facility in some embodiments to store information about the EMR accounts that reside on a particular EMR instance.

FIG. 4 is a table diagram showing sample contents of an EMR accounts table used by the facility in some embodiments to store information about the EMR accounts that reside on a particular EMR instance. This EMR accounts table 400 is for an EMR instance having the EMR instance ID WAMT. The EMR accounts table is made up of rows, such as sample rows 401-403, each representing an EMR account established in the WAMT EMR instance. Each row is divided into the following columns: an EMR username column 411 containing username for this EMR account; an EMR email column 412, containing the email address used to create this EMR account; an EMR password column 413 containing a password used to sign into the EMR account, or a hash of it; a name column 414 containing the patient name for this EMR account; a last 4 SSN column 415 containing the last four digits of the patient's social security number; a DOB column 416 containing the patient's date of birth, and an EMR record ID column 417 containing an EMR record ID identifying an EMR record in the WAMT EMR instance that the EMR account represented by the row is authorized to access. For example, row 401 represents and EMR account on the WAMT EMR instance whose EMR username is msims@outlook.com, whose email address is also msims@outlook.com, whose EMR password is contained by the table (or a hash of it), but is not shown in the figure, whose name is Marcus Sims, whose last four social security number digits are 5662, whose date of birth is Feb. 1, 2001, and which is authorized to access the EMR record on the WAMT EMR instance having EMR record ID 38000415563.

While FIG. 4 and each of the table diagrams discussed below show a table whose contents and organization are designed to make them more comprehensible by a human reader, those skilled in the art will appreciate that actual data structures used by the facility to store this information may differ from the table shown, in that they, for example, may be organized in a different manner; may contain more or less information than shown; may be compressed, encrypted, and/or indexed; may contain a much larger number of rows than shown, etc.

Figure 5:
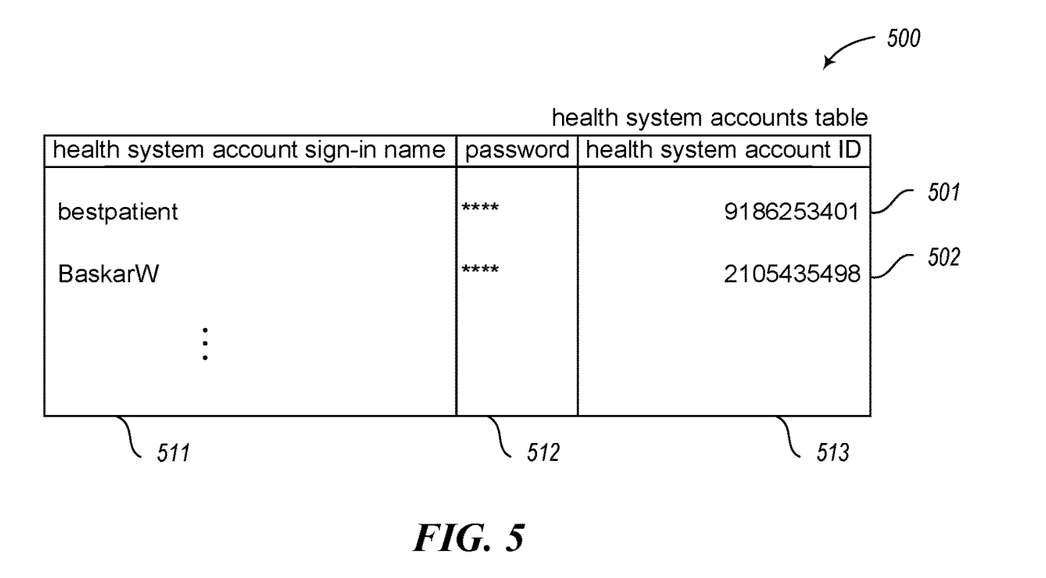
FIG. 5 is a table diagram showing sample contents of a health system accounts table used by the facility in some embodiments to store information about health system accounts.

FIG. 5 is a table diagram showing sample contents of a health system accounts table used by the facility in some embodiments to store information about health system accounts. The table 500 is made up of rows such as rows 501-502 each corresponding to a different health system account established for a patient in the health system. Each row is divided into the following columns: a health system account sign-in name column 511 containing an account name used to sign in to the health system account; a password column 512 containing a password used to sign in to the health system account or a hash of it; and a health system account ID column 513 containing an internal identifier for the health system account to which the row corresponds. For example, row 501 represents a health system account whose sign-in name is bestpatient, whose password (or a hash of it) is included in the table but not shown in the figure, and whose health system account ID is 9186253401.

Figure 6:
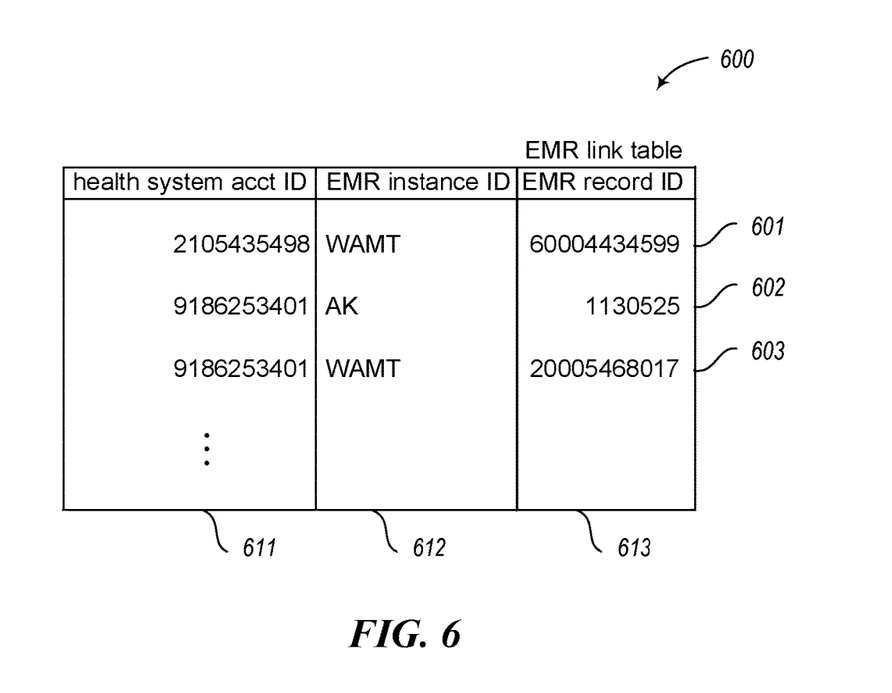
FIG. 6 is a table diagram showing sample contents of an EMR link table used by the facility in some embodiments in order to connect health system accounts of the EMR records that they are authorized to access.

FIG. 6 is a table diagram showing sample contents of an EMR link table used by the facility in some embodiments in order to connect health system accounts of the EMR records that they are authorized to access. The table is made up of rows such as 601-603 each corresponding to a different combination of a health system account and an EMR record that the health system account is authorized to access. Each row is divided into the following columns: a health system account ID column 611 containing a health system account ID identifying the health system account to which the row relates; an EMR instance ID column 612 containing an EMR instance ID identifying an EMR instance on which the EMR record to which the row relates resides; and an EMR record ID column 613 containing an EMR record ID identifying the EMR record on that EMR instance. For example, row 601 represents authorization of the health system account having health system account ID 2105435498 to access the EMR record having EMR record ID 60004434599 on the EMR instance having EMR instance ID WAMT.

Figure 7:
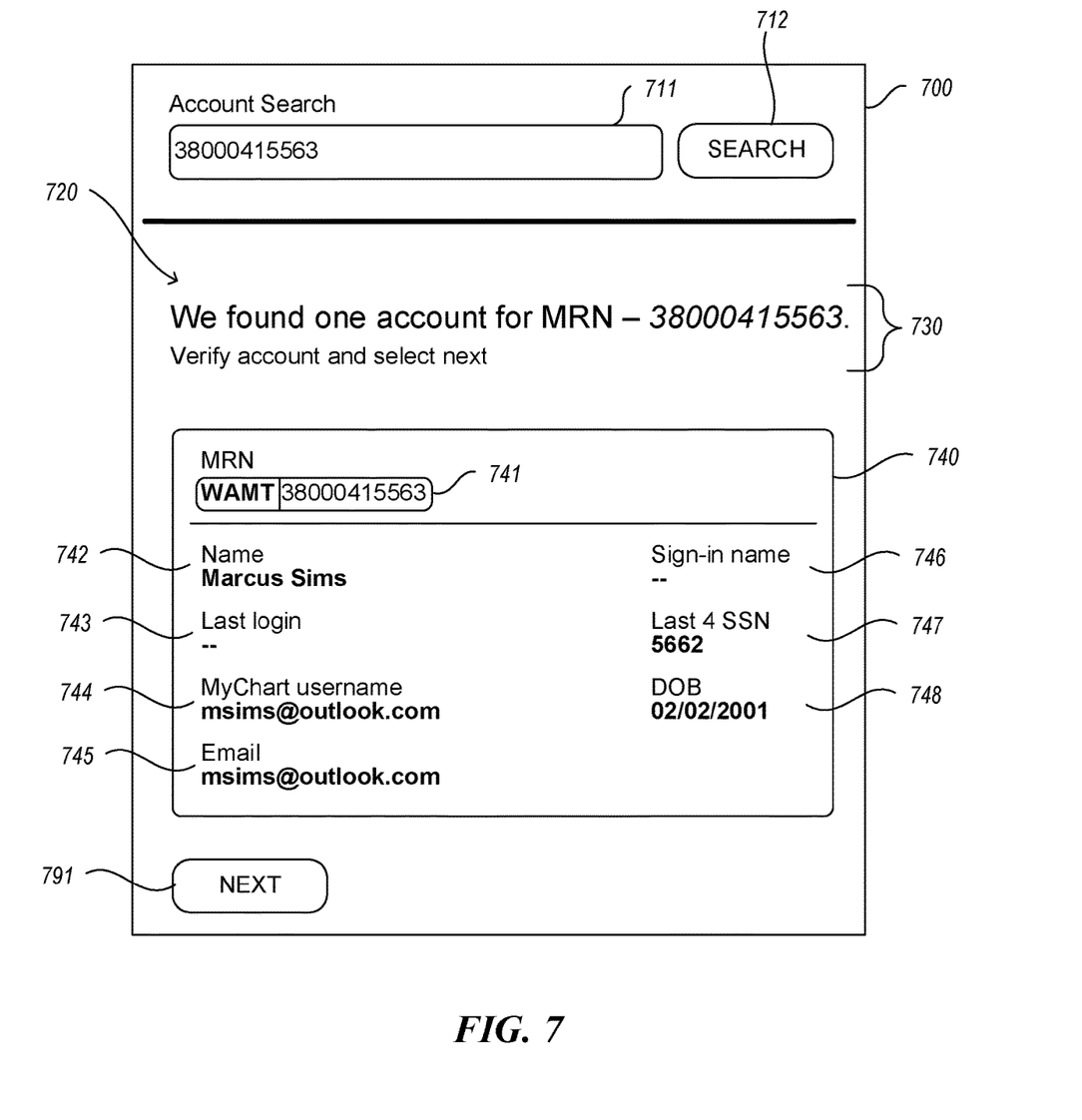
FIG. 7 is a display diagram showing a sample display presented by the facility in some embodiments in order to perform a first account search.

FIG. 7 is a display diagram showing a sample display presented by the facility in some embodiments in order to perform a first account search. The display includes a query field 711 and a search control 712. The facility user enters a query into the query field, then activates the search control in order to perform a search. Here, the search query is "38000415563". The facility then displays a search result 720. The search result includes a characterization 730 of the results of the search, as well as the single search result "card," or search result item 740. The search result item includes identifying information 741 for an EMR account including an EMR instance ID "WAMT" on the left, and MRN record ID "38000415563" on the right. The search result item further includes a patient name 742, a space 743 where the last login date and time would be displayed if it was available; an EMR account username 744, an EMR account email address 745, a space 746 where the sign-in name of a health system account would be displayed if a health system account had been found for this patient by the query; social security number 747 and date of birth 748.

By comparing the search result item 740 to the EMR accounts table 400, it can be seen that the first search has matched row 401 of the EMR accounts table, from which the facility has drawn fields 742, 744, 745, 747, and 748.

The display also includes a next control 791 that the facility user can activate in order to take action with respect to this search result item.

While FIG. 7 and each of the display diagrams discussed below show a display whose formatting, organization, informational density, etc., is best suited to certain types of display devices, those skilled in the art will appreciate that actual displays presented by the facility may differ from those shown, in that they may be optimized for particular other display devices, or have shown visual elements omitted, visual elements not shown included, visual elements reorganized, reformatted, revisualized, or shown at different levels of magnification, etc.

Figure 8:
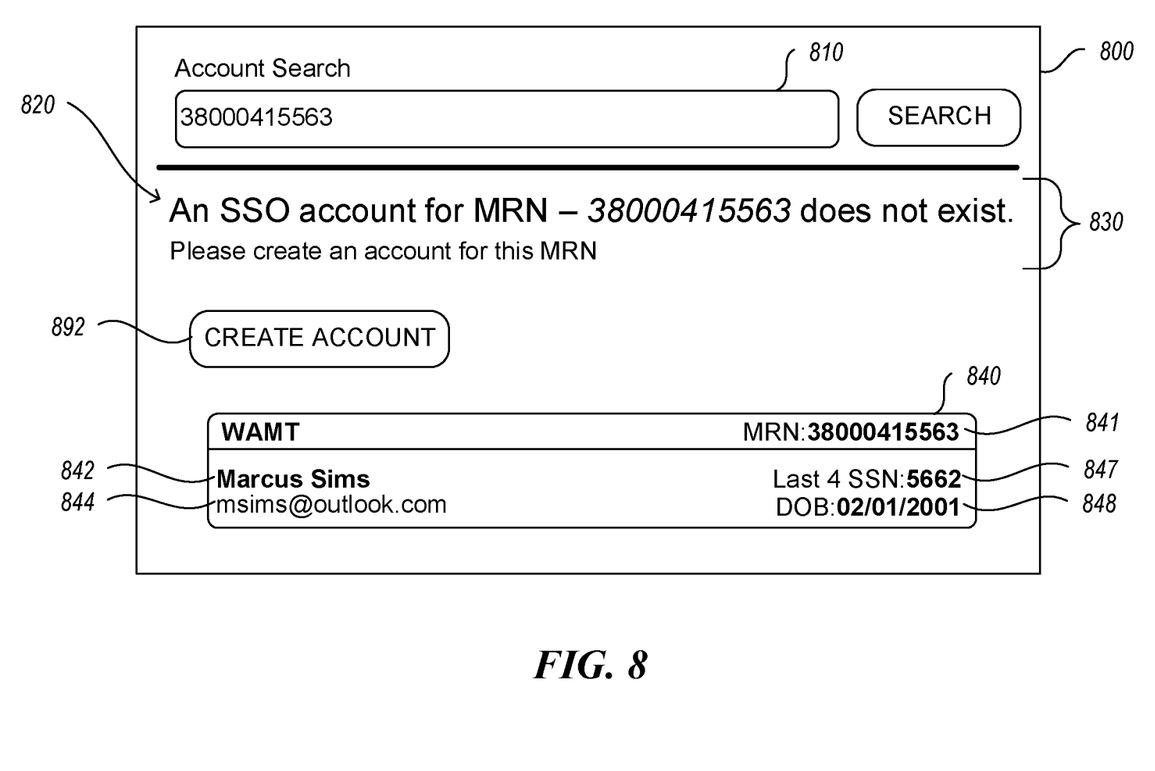
FIG. 8 is a display diagram showing sample contents of a display presented by the facility in some embodiments to take action with respect to the first account search.

FIG. 8 is a display diagram showing sample contents of a display presented by the facility in some embodiments to take action with respect to the first account search. The display 800 includes message 830 indicating that a health service account ("SSO account") does not exist for the EMR account and in EMR record identified in display 700, much of whose information is repeated in condensed search result item 840. The display includes a create account control 892 that the facility user can activate in order to create a health system account that will be authorized to access the EMR record identified in field 841, and which the patient can use to access this EMR record. In some embodiments, this process (not shown) involves creating a new row in the health system accounts table for the new health system account, and a new row in the EMR link table connecting the health system account ID contained in the new row in the health system account table to the EMR record to which the EMR account found in the first search is authorized to access. In some embodiments, the facility itself generates the health system account sign in name and password for the new row of the health system account table; in some embodiments, the facility collects this information from a person, either the facility user or the patient directly. In some embodiments, the facility extracts information about the patient from the EMR account table, the patient's EMR record, or information electronically maintained elsewhere for the patient in populating the new row of the health system accounts table.

Figure 9:
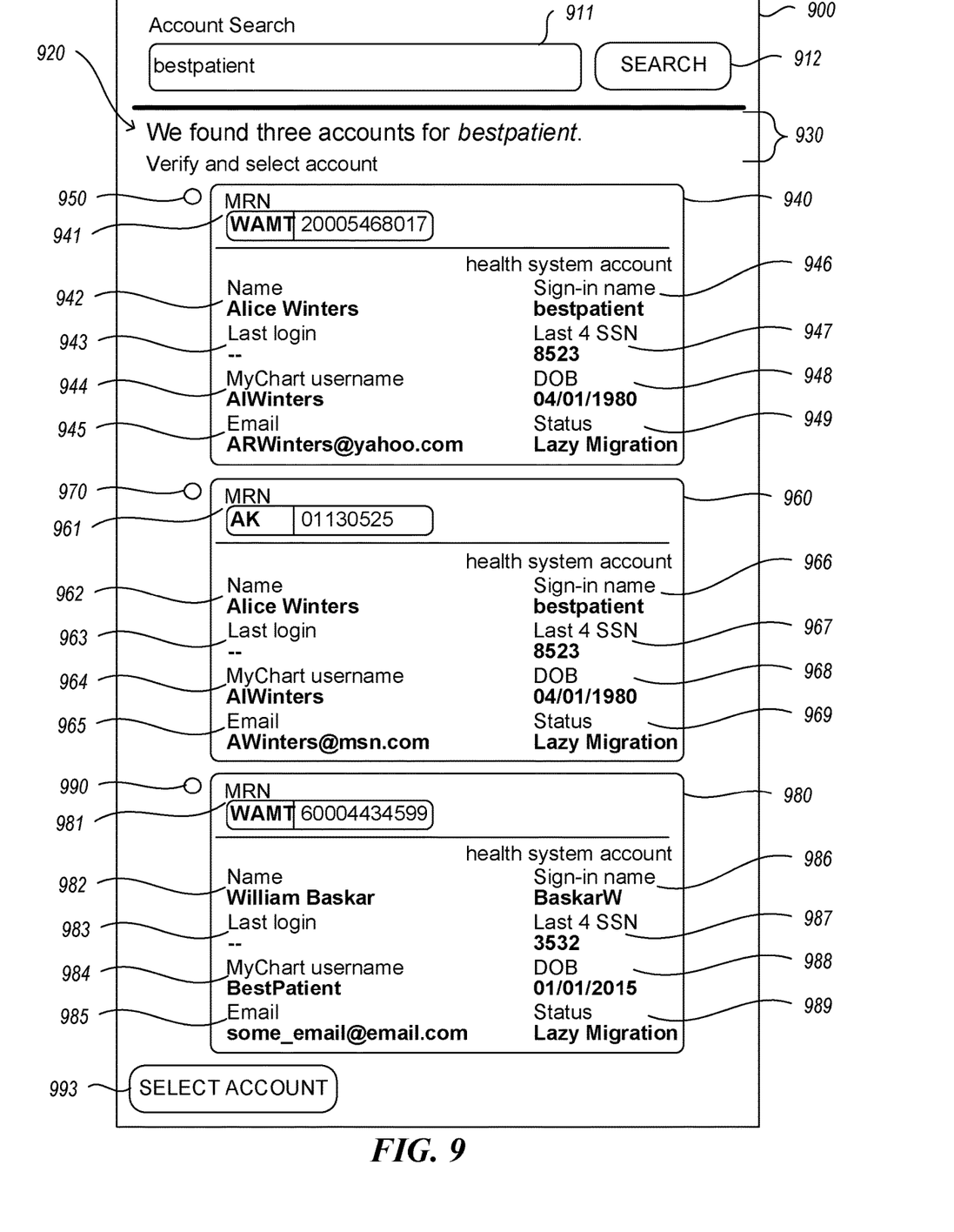
FIG. 9 is a display diagram showing sample contents of a display presented by the facility in some embodiments to display the results of a second search.

FIG. 9 is a display diagram showing sample contents of a display presented by the facility in some embodiments to display the results of a second search. The display 900 shows that the facility user has entered the query "bestpatient" into query field 911, and activated search control 912. In response, the facility has displayed search result 920, which contains three search result items 940, 960, and 980. Each of these search result items combines a health system account of a patient with an EMR account of the same patient. Search result item 940 was produced by the facility by matching the query to row 402 of the WAMT EMR table 400, as well as to row 501 of the health system accounts table 500. In response to matching row 501 of the health system accounts table, the facility joined this row of the health system accounts table with the EMR link table 600 via the health system account ID columns of those tables, to select row 603 of the EMR link table. Because row 603 of the EMR link table has the same EMR record ID—20005468017—as row 402 of the EMR accounts table, these two individual accounts were combined in search result item 940, as can be seen in details of both accounts appearing in the item.

Search result item 960 was produced by the facility by matching the query to row 501 of the health system accounts table 500, which it joined to row 603 of the EMR link table via common health system account ID 9186253401. The facility also matched the query to a row of an EMR accounts table for the EMR instance having EMR instance ID "AK", which is not shown in the figures but provides information shown in search result item 960.

The facility produced search result item 980 by matching the query to row 403 of the EMR accounts table 400 for the WAMT EMR instance. The facility further added the EMR record ID 60004434599 from row 403 of the EMR accounts table to the query, and then matched row 601 of the EMR link table 600. The facility joined row 601 of the EMR link table with row 502 of the health system accounts table 500 via common health system account ID 2105435498. Accordingly, information about these two accounts is shown in search result item 980.

The display also includes a select account control 993, which the facility user can activate after activating one of radio buttons 950, 970, and 990 to select the corresponding search result item for performing an administrative action. In some embodiments (not shown), the facility then displays a list of administrative actions to the facility user, and the facility user is able to choose one to perform with respect to the selected search result items, which the facility then performs with respect to the selected search result items.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method in a computing system, comprising:
receiving a query containing identifying information for a person;
in response to receiving the query:
processing the query against at least one first table in which each row corresponds to a different EMR account established on an EMR instance operated by a health system, and further containing an EMR record identifier identifying an EMR record on the EMR instance that the EMR account is authorized to access, to obtain a first result identifying any rows of the first table matching the query;
processing the query against a second table in which each row corresponds to a different health system account established by the health system to obtain a second result identifying any rows of the second table matching the query;
obtaining an augmented query by, for each row of the second table identified by the second result:
extracting from the row of the second table a health system account identifier;
adding the extracted a health system account identifier to the query;
processing the augmented query against a third table in which each maps a different combination of a health system account identifier and an EMR instance to an EMR record identifier identifying an EMR record on the EMR instance that the health service account is authorized to access, to obtain a third result identifying any rows of the third table matching the augmented query;
for each row of the first table identified by the first result:
where the EMR record identifier of the row of the first table matches the EMR record identifier of any row of the third table identified by the third result:
constructing a first entry comprising both information from the row of the first table and information from the row of the third table whose EMR record identifier matches and/or the row of the second table having the same health system account identifier as the row of the third table whose EMR record identifier matches;

where the EMR record identifier of the row of the first table does not match the EMR record identifier of any row of the third table identified by the third result:
constructing a second entry comprising information from the row of the first table;
for each row of the third table identified by the third result:
where no first entry contains information from the row of the third table:
constructing a third entry comprising information from the row of the third table and/or the row of the second table having the same health system account identifier as the row of the third table whose EMR record identifier matches;
causing the constructed entries to be displayed; and
soliciting user input selecting one of the displayed entries for administrative action.

2. The method of claim 1, further comprising:
performing an administrative action of, for a selected second entry:
adding a row to the second table representing a health service account authorized to access the EMR record having their EMR record identifier of the selected second entry, the row added to the second table including a health system account identifier established for the represented health service account; and
adding a row to the third table representing a mapping between the health system account identifier contained by the row added to the second table and the EMR record identifier of the selected second entry.

3. The method of claim 1, further comprising:
performing an administrative action of, for a selected third entry:
adding a row to the first table representing an EMR account, the row added to the first table containing the EMR record identifier of the selected third entry.

4. The method of claim 1, further comprising:
performing an administrative action of resetting a password corresponding to either the EMR account of the selected entry or the health system account of the selected entry.

5. The method of claim 1, further comprising:
performing an administrative action of editing contents of the row of the first table that corresponds to the selected entry, the row the second table that corresponds to the selected entry, and/or the row of the third table that corresponds to the selected entry.

6. The method of claim 1 wherein the received identifying information is one or more of:
a name of the person;
a birth date of the person;
an EMR identifier for the person;
a userid for an EMR account created for the person; or
a userid for a health system account created for the person.

7. A computing system, comprising:
one or more processors; and
one or memories collectively having contents configured to cause the processors to perform a method, the method comprising:
receiving a query containing identifying information for a person;
in response to receiving the query:
processing the query against a plurality of tables to select:
one or more first EMR record IDs each identifying an EMR record that an identified EMR account is authorized to access; and
one or more second EMR record IDs each identifying an EMR record that an identified health system account is authorized to access;
for each of the first EMR record IDs that matches a second EMR record ID, constructing an entry for the EMR account identified for the first EMR record ID and the health system account identified for the second EMR record ID;
for each of the first EMR record IDs that does not match a second EMR record ID, constructing an entry for the EMR account identified for the first EMR record ID;
for each of the second EMR record IDs that does not match a first EMR record ID, constructing an entry for the health system account identified for the second EMR record ID;
causing the constructed entries to be displayed; and
soliciting user input selecting one of the displayed entries for administrative action.

8. The computing system of claim 7, the method further comprising:
receiving first user input selecting one of the displayed entries;
in response to receiving the first user input:
soliciting user input selecting an administrative action to perform with respect to at least one of the account or accounts that the selected entry represents;
receiving second user input selecting an administrative action to perform with respect to at least one of the account or accounts that the selected entry represents; and
in response to receiving the second user input; and
performing the selected administrative action with respect to at least one of the account or accounts that the selected entry represents.

9. The computing system of claim 7, the received first user input selecting a displayed entry constructed for only an EMR account authorized to access a distinguished EMR record,
and wherein the performed administrative action is causing to be created a health system account authorized to access the distinguished EMR record.

10. The computing system of claim 7, received first user input selecting a displayed entry constructed for only a health system account authorized to access a distinguished EMR record,
and wherein the performed administrative action is causing to be created an EMR account authorized to access the distinguished EMR record.

11. The computing system of claim 7, the received first user input selecting a displayed entry representing constructed for both a distinguished EMR account and a distinguished health system account,
and wherein the performed administrative action is causing to be revised both first information stored by one or more tables of the plurality of tables for the distinguished EMR account and second information stored by one or more tables of the plurality of tables for the distinguished health system account.

12. The computing system of claim 7 wherein the performed administrative action is causing a password established for an account for which the entry selected by the first user input was constructed to be reset.

13. One or memories collectively having contents configured to cause a computing system to perform a method, the method comprising:
receiving a query containing identifying information for a person;
in response to receiving the query:
processing the query against a plurality of tables to select:
one or more first EMR record IDs each identifying an EMR record that an identified EMR account is authorized to access; and
one or more second EMR record IDs each identifying an EMR record that an identified health system account is authorized to access;
for each of the first EMR record IDs that matches a second EMR record ID, constructing an entry for the EMR account identified for the first EMR record ID and the health system account identified for the second EMR record ID;
for each of the first EMR record IDs that does not match a second EMR record ID, constructing an entry for the EMR account identified for the first EMR record ID;
for each of the second EMR record IDs that does not match a first EMR record ID, constructing an entry for the health system account identified for the second EMR record ID;
causing the constructed entries to be displayed; and
soliciting user input selecting one of the displayed entries for administrative action.

14. The one or more memories of claim 13, the method further comprising:
receiving first user input selecting one of the displayed entries;
in response to receiving the first user input:
soliciting user input selecting an administrative action to perform with respect to at least one of the account or accounts that the selected entry represents;
receiving second user input selecting an administrative action to perform with respect to at least one of the account or accounts that the selected entry represents; and
in response to receiving the second user input; and
performing the selected administrative action with respect to at least one of the account or accounts that the selected entry represents.

15. The one or more memories of claim 13, the received first user input selecting a displayed entry constructed for only an EMR account authorized to access a distinguished EMR record,
and wherein the performed administrative action is causing to be created a health system account authorized to access the distinguished EMR record.

16. The one or more memories of claim 13, received first user input selecting a displayed entry constructed for only a health system account authorized to access a distinguished EMR record,
and wherein the performed administrative action is causing to be created an EMR account authorized to access the distinguished EMR record.

17. The one or more memories of claim 13, the received first user input selecting a displayed entry representing constructed for both a distinguished EMR account and a distinguished health system account,
and wherein the performed administrative action is causing to be revised both first information stored by one or more tables of the plurality of tables for the distinguished EMR account and second information stored by one or more tables of the plurality of tables for the distinguished health system account.

18. The one or more memories of claim 13 wherein the performed administrative action is causing a password established for an account for which the entry selected by the first user input was constructed to be reset.

* * * * *